Figure 1:
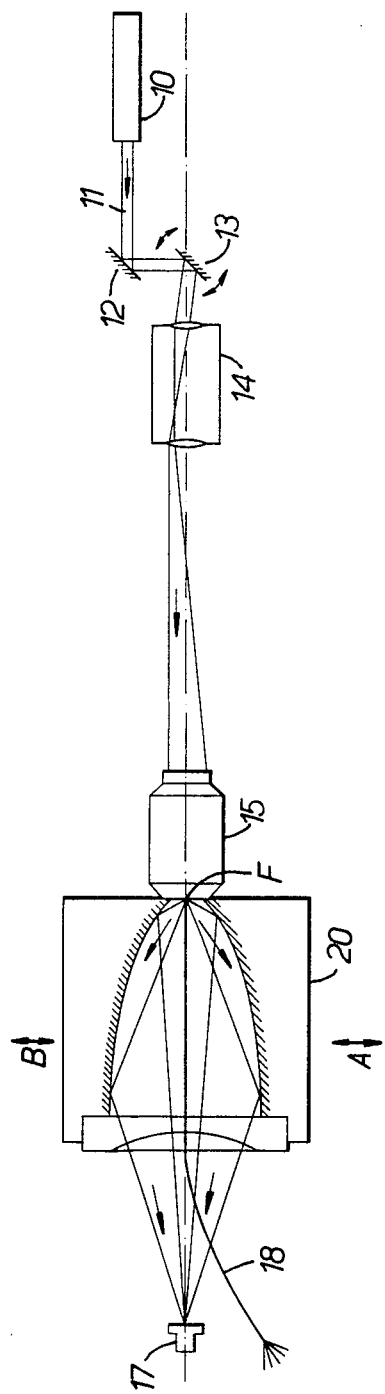

United States Patent [19]

Reid et al.

[11] Patent Number: 4,551,020
[45] Date of Patent: Nov. 5, 1985

[54] OPTICAL APPARATUS FOR DETERMINING THE INDEX PROFILE OF AN OPTICAL FIBRE

[75] Inventors: Douglas C. J. Reid, Rugby; William J. Stewart, Fritwell, both of England

[73] Assignee: Plessey Overseas Limited, Ilford, England

[21] Appl. No.: 375,662

[22] Filed: May 6, 1982

[30] Foreign Application Priority Data

May 7, 1981 [GB] United Kingdom ............. 8113896

[51] Int. Cl.⁴ .................... G01N 21/41; G01N 21/84
[52] U.S. Cl. .................................. 356/73.1; 356/128
[58] Field of Search ........................... 356/73.1, 128

[56] References Cited

U.S. PATENT DOCUMENTS 4,349,276 9/1982 DiVita ........................ 356/73.1

Primary Examiner—Vincent P. McGraw
Attorney, Agent, or Firm—Fleit, Jacobson, Cohn & Price

[57] ABSTRACT

Optical apparatus for determining for example by display on an oscilloscope the refractive index profile across an optical fibre including an ellipsoidal reflector and a scanning system for a laser beam directed towards one focus of the ellipsoidal reflector at which point the fibre to be examined is placed and including a detector which is relatively small in size situated at the other focus of the ellipsoidal reflector.

6 Claims, 4 Drawing Figures

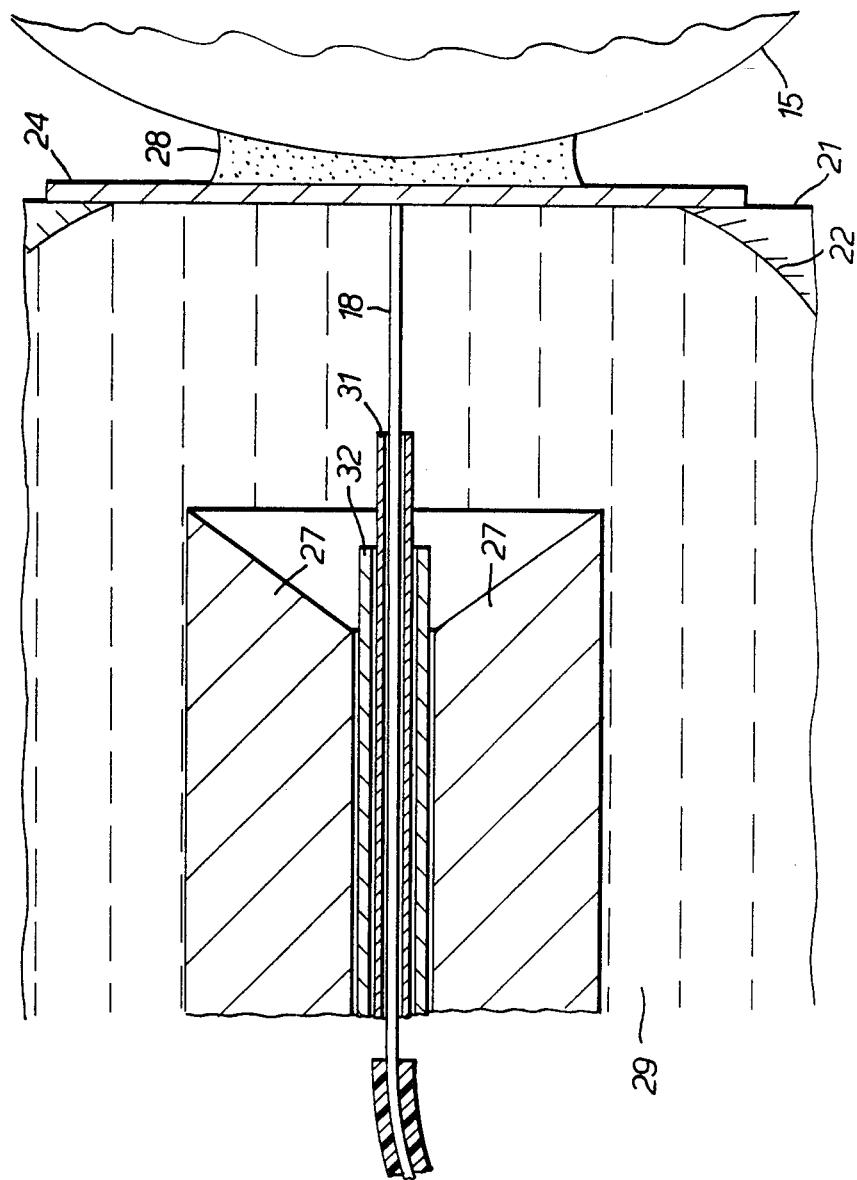

OPTICAL APPARATUS FOR DETERMINING THE INDEX PROFILE OF AN OPTICAL FIBRE

The present invention relates to optical apparatus and more particularly to a high resolution optical apparatus for the examination of the profiling of optical fibres.

Optical fibres for use in the transmission of data are manufactured with a defined refractive index profile across the diameter of the fibre. The transmission characteristic of the optical fibre is determined by the quality of the glass and also by the accuracy of the refractive index profiling. It is therefore important in assessing the probable transmission characteristics of a particular optical fibre to be able to accurately determine the refractive index profiling of the fibre. Since fibers are normally drawn from a glass preform the profile characteristic of each fibre will not vary substantially along the length of the fibre and therefore an accurate picture of the characteristic of each fibre can be obtained by an examination of the end portion of the length of fibre.

The present invention provides an apparatus for accurately determining the index profile of an optical fibre in a relatively short period of time.

According to the present invention there is provided an optical apparatus for determining the index profile of an optical fibre including an elliptical reflector, means for holding an optical fibre the index profile of which is to be determined in a position along the major axis of the ellipse with the end of the fibre being positioned at one of the foci of said ellipse, means for scanning a beam of light across the surface of said end of said fibre and means at the opposite end of said elliptical reflector for collecting said light reflected by said reflector.

In a particular embodiment the elliptical reflector is filled with an index matching fluid and equipped with associated sealing means for retaining said fluid and with means for topping up said reflector to compensate for any fluid loss.

The optical fibre is preferably mounted inside one or more tubes which are accurately aligned with the axis of the elliptical reflector.

Figure 4:
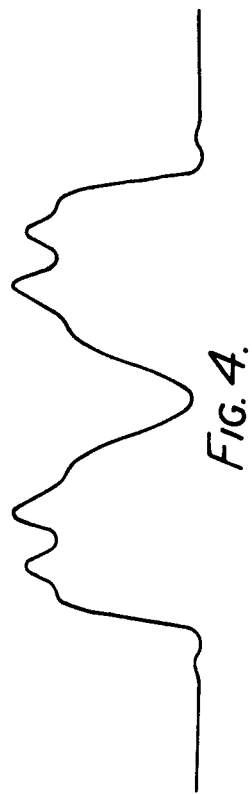
Figure 2:
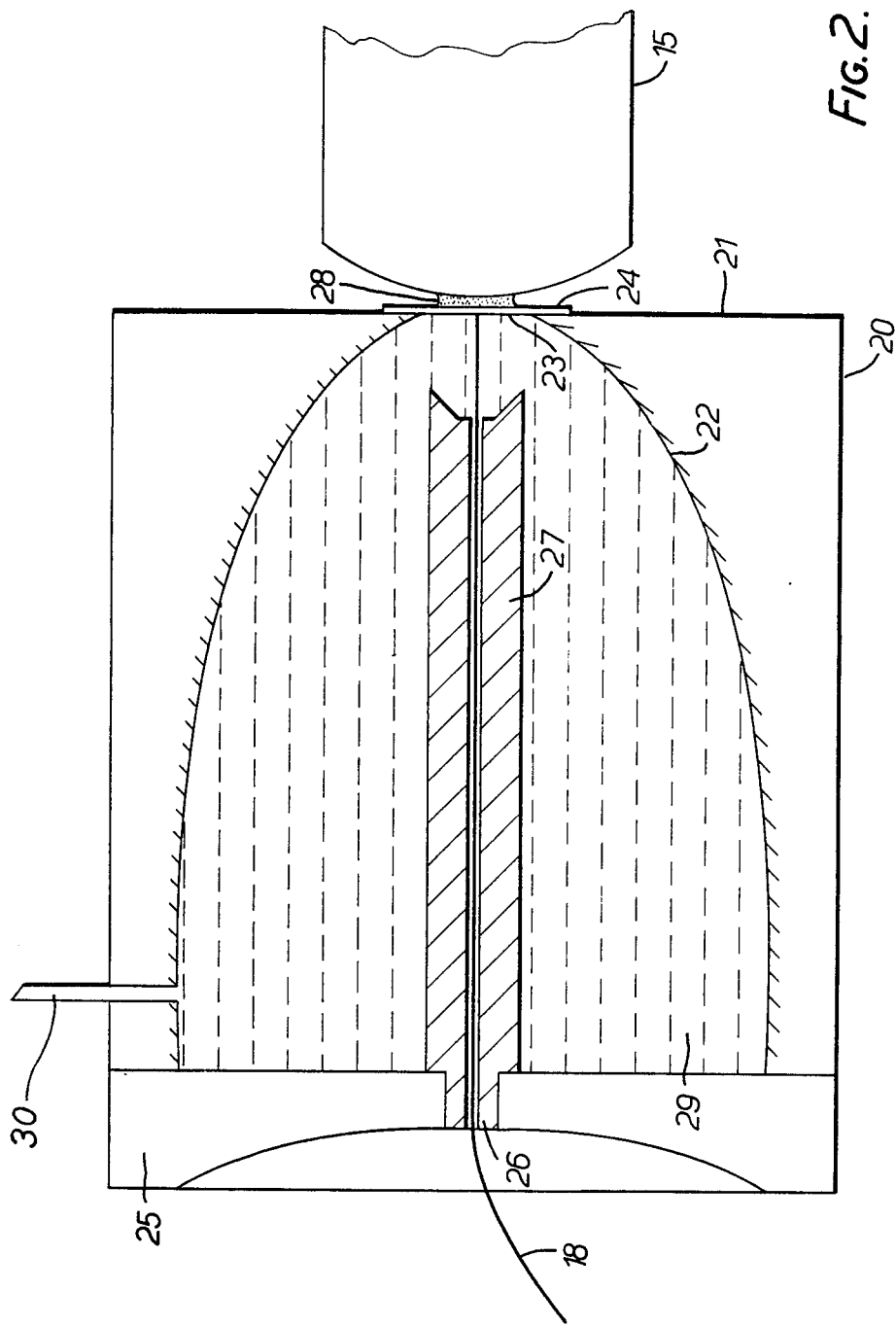

Embodiments of the present invention will now be described, by way of example with reference to the accompanying drawings in which:

FIG. 1 shows optical apparatus for determining the index profile of an optical fibre according to the present invention, FIG. 2 shows the elliptical mirror and fibre retention means of FIG. 1 in greater detail FIG. 3 shows the fibre retention means of FIG. 2 in greater detail and, FIG. 4 shows an index profile of a single mode fibre produced by the optical apparatus of the present invention.

Referring now to FIG. 1 of the drawings, there is shown a light source 10 which is preferably a laser producing a beam of illumination 11 which is reflected by first and second scanning mirrors 12 and 13 and focussed by first and second focussing optics 14, 15 prior to entering an elliptical reflector cell 20 (see FIGS. 2 and 3 for greater detail). The light is internally reflected within the cell and is collected by a photodetector 17. An optical fibre 18 is mounted within the cell 20 as shown in greater detail in FIG. 2 with the end of the fibre being positioned at a point F which is one of the foci of the elliptical reflector.

In operation the laser beam is scanned across the end face of the optical fibre situated at point F by the scanning mirror system 12, 13 and an output is taken from the detector 17 which by suitable processing produces an index profile such as shown in FIG. 4 on an oscilloscope.

Referring now to FIG. 2 the design of the elliptical reflector cell 20 is shown in greater detail. The cell may be constructed from a electro formed mirror 22 retained within a solid block of epoxy resin 21.

The end of the block 21 is machined down to produce an opening 23 which is closed by a glass microscope cover slip 24. The opposite end of the cell is closed by a transparent window 25 which has a hole 26 through which the optical fibre 18, whose index profile is to be determined, is inserted, The fibre 18 is held in position along the axis of the ellipsoidal cell by an axial tube 27 attached to the perspex window 25 and by further reduction tubes as shown in FIG. 3.

The second focussing optical system is an oil immersion microscope objective to provide high resolution.

Thus between the cover plate 24 and the focussing optical system 15 a layer of oil 28 is present. The entire inside of the cell 20 is filled with index matching fluid 29. The fluid 29 is inserted via tube 30 which is connected to a reservoir (not shown) so that any fluid escaping between the fibre 18 and the support tube 27 is compensated for.

It is important that the fibre 18 is held substantially rigidly in the centre of the cover slip 24 and abutting the inside surface of the slip. This is accomplished as shown in FIG. 3. The fibre 18 is prepared by stripping the outer protective plastic layer and cutting the fibre to produce a square end. The fibre is then inserted within a thin flexible hollow needle 31 and the two are inserted inside a stiffer hollow tube 32 which in turn is inserted into the support tube 27.

The scale of the drawing in FIG. 3 is large and the fibre 18, the end of which is made as flat as possible, is therefore positioned very accurately in relation to the cover slip 24 and hence the optics 15.

A small amount of fluid escapes past the fibre 18 and the tubes 31, 32 and 27 and this is replaced as describrd above. The fibre can thus easily be withdrawn and replaced by a further fibre for examination.

The transparent window 25 can preferably be formed with a concave outer surface the radius of which is equal to the distance between it and the detector 17. This keeps the collected spot small.

Additionally the inner surface can also be curved parallel to the concave surface to form a plano meniscus window. If the cell is used in a vertical axis any bubbles formed in the oil will tend to float to the outside edge of the window.

Referring now to FIG. 4 the index profile across a fibre as shown in FIG. 4 is seen to be an accurate picture of the index profile across a single mode optical fibre of 8 $\mu$m core diameter.

The apparatus shown in the above embodiments can be used to examine other objects where the refractive index varies across the width providing that suitable means are provided to retain such objects in the required position substantially at the focus of the ellipse.

The advantage of the above apparatus is that the detector can be relatively small due to the focussing properties of the elliptical reflector.

The inside of the cell is filled as described with a liquid which makes the numerical aperture of the cell approximately 1.3. No external optics are required between the cell and the detector. The mirror also inverts the beam centre-to-edge so that the circular blocking stop is replaced by a conventional iris (not shown) between the detector and the transparent window 25.

FIG. 4 shows results using a Helium-Neon (He-Ne) laser (wavelength=0.6328 μm) and a blocking NA 0.96. The rise at the right hand edge of FIG. 4 shows the graded core required by a multimode fibre. The 20%-80% risdistance (Rayleigh resolution) for FIG. 4 is about 0.3 μm (~λ/2) or about 2.5 times better than results obtained in practise by previously known methods and apparatus.

Referring again to FIG. 1, arrows A and B illustrate a further embodiment in which the cell 20 may be scanned by movement of the entire cell across the light beam.

In this embodiment the mirrors 12 and 13 are set in a fixed position such that beam 11 passes along the axis of the optical system defined by lenses 14 and 15. To obtain a profile across the fibre the cell 20 is scanned in a first direction as indicated by arrows A and B and the output of detector 17 is displayed on an oscilloscope or chart recorder etc.

To obtain a profile map of the entire end surface of a fibre the cell 20 may be arranged to be scanned in a direction which is both orthogonal to the direction indicated by the arrows A and B and perpendicular to the plane of the paper. For example to obtain a display on an oscilloscope the scan frequency in one direction is made considerably higher than that in the other direction this providing a raster scan. The physical position of the cell is space at each instant can be determined and linked into the X,Y inputs of the oscilloscope to provide a reference signal for correction of the displayed picture of the profile of the complete end area of the fibre.

What we claim is:

1. Optical apparatus for determning the index profile of an optical fibre, said optical apparatus comprising an elliptical reflector, means for holding an optical fibre, the index profile of which is to be determined in a position along the major axis of the ellipse, with the end of the fibre being positioned at one of the foci of said elliptical reflector, means for scanning a beam of light across the surface of said end of said fibre and means located at another focus of said elliptical reflector for detecting said beam of light reflected by said elliptical reflector.

2. Optical apparatus as claimed in claim 1 in which the elliptical reflector is filled with an index matching fluid and equipped with associated sealing means for retaining said fluid and with means for topping up said reflector to compensate for any fluid loss.

3. Optical apparatus as claimed in claim 1 in which the optical fibre, the index profile of which is to be determined is mounted inside one or more tubes which are accurately aligned with the axis of the elliptical reflector.

4. Optical apparatus as claimed in claim 1 in which the means for detecting the light reflected by said reflector is a single photodetector.

5. Optical apparatus as claimed in claim 1 in which the means for scanning the beam of light across the surface of the end of the fibre comprises means for moving the elliptical reflector across the light beam in a controlled manner.

6. Optical apparatus as claimed in claim 1 in which the light beam used to scan the optical fibre passes through an oil immersion objective to achieve a pin point focus onto the end of the optical fibre.

* * * * *